US009089131B2

(12) United States Patent
Swanzy et al.

(10) Patent No.: US 9,089,131 B2
(45) Date of Patent: Jul. 28, 2015

(54) PRESERVATIVE SYSTEM

(71) Applicant: Mary Kay Inc., Dallas, TX (US)

(72) Inventors: James Swanzy, Arlington, TX (US);
Leslie Lockhart, Dallas, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 14/204,454

(22) Filed: Mar. 11, 2014

(65) Prior Publication Data

US 2014/0274974 A1    Sep. 18, 2014

Related U.S. Application Data

(60) Provisional application No. 61/777,639, filed on Mar. 12, 2013.

(51) Int. Cl.
*A01N 37/36* (2006.01)
*A01N 37/40* (2006.01)
*A01N 31/02* (2006.01)

(52) U.S. Cl.
CPC ............... *A01N 37/40* (2013.01); *A01N 31/02* (2013.01)

(58) Field of Classification Search
CPC ... A61K 31/60; A61K 31/603; A61K 31/618; A01N 37/40
USPC .......................................... 514/159
See application file for complete search history.

(56) References Cited

U.S. PATENT DOCUMENTS

| | | | |
|---|---|---|---|
| 2,081,117 A | 5/1937 | Hall | 424/60 |
| 2,113,374 A * | 4/1938 | Hall | 562/473 |
| 2,279,468 A | 4/1942 | Lahousse et al. | 424/60 |
| 3,949,087 A | 4/1976 | Bacq et al. | 514/561 |
| 4,009,254 A | 2/1977 | Renold | 424/59 |
| 4,271,176 A * | 6/1981 | Berke et al. | 514/390 |
| 4,723,420 A | 2/1988 | Sitte | 62/51.1 |
| 4,839,159 A | 6/1989 | Winter et al. | 424/59 |
| 5,045,306 A | 9/1991 | Cavazza et al. | 424/54 |
| 5,258,552 A | 11/1993 | Cavazza et al. | 564/197 |
| 5,314,689 A | 5/1994 | Scandurra et al. | 424/433 |
| 5,637,305 A | 6/1997 | Cavazza et al. | 424/401 |
| 5,667,791 A | 9/1997 | Hersh et al. | 424/401 |
| 5,827,886 A | 10/1998 | Hersh | 514/562 |
| 5,843,476 A | 12/1998 | Ribier et al. | 424/450 |
| 5,853,705 A | 12/1998 | Nakayama et al. | 424/59 |
| 5,925,369 A | 7/1999 | Scafetta et al. | 424/405 |
| 5,962,000 A | 10/1999 | Yanagida et al. | 424/401 |
| 6,051,245 A | 4/2000 | Chaudhry et al. | 424/401 |
| 6,284,234 B1 | 9/2001 | Niemiec et al. | 424/78.07 |
| 6,337,320 B1 | 1/2002 | Hersh et al. | 514/18 |
| 6,372,791 B1 | 4/2002 | Shapiro et al. | 514/557 |
| 6,376,557 B1 | 4/2002 | Zaveri | 424/725 |
| 6,432,424 B1 | 8/2002 | Shapiro et al. | 424/401 |
| 6,495,126 B1 | 12/2002 | Schlitz | 424/78.02 |
| 6,497,889 B2 | 12/2002 | Takekoshi et al. | 424/401 |
| 6,573,299 B1 | 6/2003 | Petrus | 514/558 |
| 6,585,987 B1 | 7/2003 | Fransoni | 424/401 |
| 6,649,176 B1 | 11/2003 | Shapiro et al. | 424/401 |
| 6,761,903 B2 | 7/2004 | Chen et al. | 424/451 |
| 6,762,158 B2 | 7/2004 | Lukenbach et al. | 510/122 |
| 6,835,392 B2 | 12/2004 | Hsu et al. | 424/449 |
| 6,908,889 B2 | 6/2005 | Niemiec et al. | 510/130 |
| 6,984,390 B2 | 1/2006 | Sakuta | 424/401 |
| 6,987,120 B1 | 1/2006 | Del Soldato | 514/365 |
| 7,932,417 B2 * | 4/2011 | Mentlik et al. | 560/8 |
| 8,258,121 B2 | 9/2012 | Mentlik et al. | 514/159 |
| 2003/0147968 A1 | 8/2003 | Farber | 424/523 |
| 2003/0157137 A1 | 8/2003 | Farber | 424/401 |
| 2004/0146539 A1 | 7/2004 | Gupta | 424/401 |
| 2004/0161435 A1 | 8/2004 | Gupta | 424/401 |
| 2004/0191330 A1 | 9/2004 | Keefe et al. | 424/638 |
| 2005/0069598 A1 | 3/2005 | Ribnicky et al. | 424/740 |
| 2005/0100519 A1 | 5/2005 | Guth et al. | 424/62 |
| 2005/0158258 A1 | 7/2005 | Fisher | 424/63 |
| 2005/0214333 A1 | 9/2005 | Lanzendoerfer et al. | 424/401 |
| 2005/0220728 A1 | 10/2005 | Kanji et al. | 424/59 |
| 2005/0261242 A1 | 11/2005 | Soldato | 514/56 |
| 2005/0266057 A1 | 12/2005 | Hagura et al. | 424/443 |
| 2006/0002876 A1 | 1/2006 | Cahen | 424/70.1 |
| 2006/0029657 A1 | 2/2006 | Popp et al. | 424/450 |
| 2011/0159126 A1 | 6/2011 | Tai | 424/758 |
| 2012/0053133 A1 | 3/2012 | Kanatani et al. | 514/23 |
| 2012/0083497 A1 | 4/2012 | Riggs et al. | 514/239.5 |

FOREIGN PATENT DOCUMENTS

| | | |
|---|---|---|
| DE | 126311 | 11/1901 |
| EP | 0629347 | 12/1994 |
| EP | 1421940 | 5/2004 |
| FR | 1254002 | 1/1961 |
| GB | 2283173 | 5/1995 |
| JP | 2012-163397 | 8/2012 |
| RU | 2 294 167 | 9/2006 |
| WO | WO 02/26207 | 4/2002 |

OTHER PUBLICATIONS

PCT International Search Report and Written Opinion, issued in International Application No. PCT/US2007/069160, dated Oct. 23, 2007.

International Preliminary Report on Patentability, issued in Int. App. No. PCT/US2007/069160, mail date Dec. 4, 2008.

Office Communication, issued in European Patent Application No. 07 762 239.7, dated Oct. 11, 2010.

Djurendic et al., CAS accession No. 2000:779843, corresponding to Djurendic et al., Journal of the Serbian Chemical Society, 65:681-689, 2000.

(Continued)

*Primary Examiner* — Kevin E Weddington

(74) *Attorney, Agent, or Firm* — Norton Rose Fulbright US LLP

(57) ABSTRACT

Disclosed is a preservative or antimicrobial system, and methods for its use, that includes at least one ester of salicylic acid and glycerin or a salt thereof.

24 Claims, 2 Drawing Sheets

(56) References Cited

OTHER PUBLICATIONS

Ishihara et al., "An extremely simple, convenient, and selective method for acetylating primary alcohols in the presence of secondary alcohols," *Journal of Organic Chemistry*, 58:3791-3793, 1993.
Office Communication, issued in Chinese Patent Application No. 200780018364, dated Aug. 4, 2010. (English Translation).
Office Communication, issued in Eurasian Patent Application No. 200802364, dated Mar. 5, 2011. (English Summary).
Office Communication, issued in European Patent Application No. 07 762 239.7, dated Mar. 18, 2010.
Office Communication, issued in U.S. Appl. No. 11/749,869, dated Sep. 8, 2010.
Office Communication, issued in U.S. Appl. No. 11/749,869, dated Jun. 3, 2010.
Office Communication, issued in U.S. Appl. No. 11/749,869, dated Oct. 26, 2009.
Office Communication, issued in U.S. Appl. No. 11/749,869, dated Jun. 5, 2009.
Office Communication, issued in U.S. Appl. No. 11/749,869, dated Feb. 13, 2009.
Office Communication, issued in U.S. Appl. No. 11/749,869, dated Sep. 4, 2008.
Office Communication issued in Ukrainian Patent Application No. 2008 14596, dated Aug. 2, 2011. (English translation).
Search Report and Written Opinion issued in PCT/US2014/023527, dated Jul. 17, 2014.

* cited by examiner

PRESERVATIVE SYSTEM

CROSS-REFERENCE TO RELATED APPLICATIONS

This application claims the benefit of U.S. Provisional Application No. 61/777,639, filed Mar. 12, 2013. The contents of the reference application are incorporated into the present application by reference.

BACKGROUND OF THE INVENTION

A. Field of the Invention

The present invention relates generally to a preservative or anti-microbial system that can be used to inhibit the growth of microorganisms. The preservative or anti-microbial system can be used in a variety of applications (e.g., in topical formulations such as cosmetic or pharmaceutical formulations, cleansing or disinfectant formulations for hard surfaces or for skin or for skin wounds, food formulations, etc.). The preservative or anti-microbial system includes a mixture of esters from glycerol and salicylic acid.

B. Description of Related Art

There are several preservative/anti-microbial systems currently available. Examples of such systems generally include parabens (e.g., methylparaben, ethylparaben, propylparaben, benzylparaben, butylparaben, etc.), which are useful against gram-positive bacteria, isopropynylbutylcarbamate (IPBC), which is useful against mold, imidazolidinyl urea, which is used full against gram-negative bacteria, methylisothiazolinone (MIT), which is useful against gram-negative bacteria, chlorphenesin, which is useful against mold, benzoic acid, which is useful against gram-positive bacteria, yeast, and mold, and caprylyl glycol, which is useful against gram negative bacteria. While these systems are useful in inhibiting the growth of various types of microorganisms, several have drawbacks ranging from toxicity to difficulties in using them to formulate compositions.

One potential alternative to chemical preservatives is to use natural ingredients. However, such ingredients can be costly, not as effective, and can actually be caustic or irritating to skin if used in effective amounts. For instance, Amipreserve by Alban Muller International is a pure natural salicylic acid that is extracted from wintergreen leaves. The maximum recommended amount of Amipreserve to include in a given formulation is 0.5 wt % due to the caustic effects of salicylic acid—in particular the free carboxylic acid group of this molecule. Therefore, additional preservatives or anti-microbial agents are needed in the formulation to effectively inhibit microorganism growth.

As another example, caprylyl glycol is difficult to use with emulsions. In particular, caprylyl glycol can destabilize emulsions by interfering with the interface between the continuous and discontinuous phases of said emulsion. Therefore, it can be difficult to formulate with and oftentimes it has to be added to the formulation post emulsification. Such a procedure adds additional process steps, complexity, and costs to preparing the emulsion.

Oftentimes, in order to produce a broad spectrum preservative or anti-microbial system, several different types of preservatives have to be combined. This increases the costs of the preservative system, adds additional ingredients to the formulation, and can potentially affect the stability of the formulation.

SUMMARY OF THE INVENTION

It has been discovered that a mixture of esters of glycerol and salicylic acid provides an effective preservative or antimicrobial system. This system can be used in all types of formulations (e.g. cosmetic, pharmaceutical, cleansing, disinfecting, debridement, food formulations, etc.). Further, the esterification of the salicylic acid molecule with the glycerol molecule reduces the caustic effects of the salicylic acid by effectively neutralizing its carboxylic acid group. Also, the presence of glycerol can have a soothing effect on skin. This allows for the inclusion of more of the preservative or anti-microbial system into a given formulation while avoiding the caustic side effects seen with other preservative systems having a free carboxylic acid group. Further, the number of additional preservatives in the formulation can be reduced or eliminated altogether.

The data suggests that the preservative or anti-microbial system of the present invention is effective in inhibiting growth of various gram-positive bacteria, fermentative gram-negative bacteria, and yeast within 5 to 7 days from initial inoculation or infection of said microorganisms. Even further, the combination of the mixtures of the esters of salicylic acid and glycerin with imidazolidinyl urea shows synergistic and surprising properties in that each individually were found incapable of inhibiting various oxidative gram negative bacteria and mold within 5 to 7 days from initial inoculation or infection, but when combined were capable of inhibiting such microorganisms. Therefore, the combination of the mixture of the esters of salicylic acid and glycerin with imidazolidinyl urea can result in an effective broad spectrum preservative or antimicrobial system.

In one particular aspect, there is disclosed a preservative or anti-microbial system comprising at least one ester of salicylic acid and glycerin or a salt thereof. The at least one ester of salicylic acid and glycerin can have any one of the following formulas:

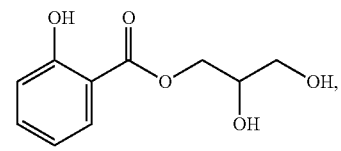

(1 glycerol mono-salicylate)

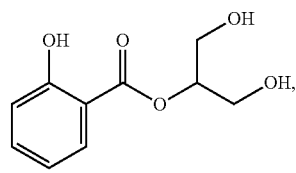

(2 glycerol mono-salicylate)

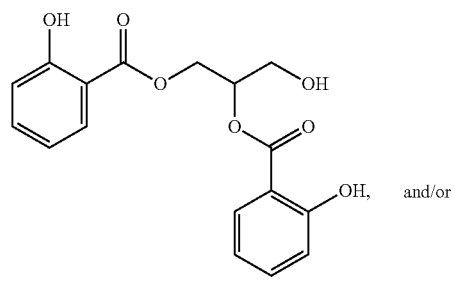

and/or (1,2 glycerol di-salicylate)

-continued

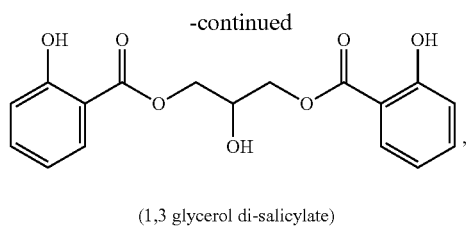

(1,3 glycerol di-salicylate)

or salts thereof or modifications thereof or derivatives thereof. In particular instances, the preservative or anti-microbial system can include at least two, three, or all four of said esters of salicylic acid and glycerin or salts thereof. In some instances, the combination includes 1 glycerol mono-salicylate and 2 glycerol mono-salicylate. In another instance, the combination includes 1 glycerol mono-salicylate and 1,2 glycerol di-salicylate. In a further instance, the combination includes 1 glycerol mono-salicylate and 1,3 glycerol di-salicylate. In another instance, the combination includes 2 glycerol mono-salicylate and 1,2 glycerol di-salicylate. A further combination includes 2 glycerol mono-salicylate and 1,3 glycerol di-salicylate. An even further combination includes 1,2 glycerol di-salicylate and 1,3 glycerol di-salicylate. A further combination includes 1 glycerol mono-salicylate, 2 glycerol mono-salicylate, and 1,2 glycerol di-salicylate. Another combination includes 1 glycerol mono-salicylate, 2 glycerol mono-salicylate, and 1,3 glycerol di-salicylate. A further combination includes 1 glycerol mono-salicylate, 1,2 glycerol di-salicylate, and 1,3 glycerol di-salicylate. Another combination includes 2 glycerol mono-salicylate, 1,2 glycerol di-salicylate, and 1,3 glycerol di-salicylate. Another combination includes 1 glycerol mono-salicylate, 2 glycerol mono-salicylate, 1,2 glycerol di-salicylate, and 1,3 glycerol di-salicylate. In particular embodiments, the combination of the mixtures of esters of salicylic acid and glycerin is 1 glycerol mono-salicylate, 2 glycerol mono-salicylate, 1,2 glycerol di-salicylate, and 1,3 glycerol di-salicylate. Further, the mixture can also include glycerin, salicylic acid, and/or methyl salicylate. In other instances, the mixture can exclude any one of or all of glycerin, salicylic acid, and/or methyl salicylate. The amount of each of the esters of salicylic acid and glycerol can be varied as desired. In certain aspects, the amounts within the mixture can be from 30 to 60 wt % of 1 glyceryl mono-salicylate, 1 to 5 wt % of 2 glyceryl mono-salicylate, 1 to 6 wt % of 1,2 glyceryl di-salicylate, and/or 10 to 25 wt % of 1,3 glyceryl di-salicylate. Further, the mixture can also include glycerin at amounts ranging from 10 to 25 wt % and/or salicylic acid at amounts ranging from 1 to 6 wt %. Alternatively, the total amount of esters of salicylic acid and glycerol within a mixture can range from 50 wt % to 100 wt % or from 50 wt % to 90 wt % or from 60 wt % to 80 wt % or from 50, 55, 60, 65, 70, 75, 80, 85, 90, 95 wt % or more within the mixture. The mixture can then be used in a formulation as a preservative or antimicrobial system in amounts ranging from 0.01 to 10 wt % or from 0.1 to 5 wt % or from 1 to 3 wt % within the formulation or as needed to preserve a given formulation or inhibit microorganism growth in a formulation. In some aspects, the amount of the preservative or anti-microbial system of the present invention within a given formulation can be from 0.01, 0.1, 1, 2, 3, 4, 5, 6, 7, 8, 9, 10, 15, 20, 25, 30, 35% or more by weight within a given formulation. The preservative or anti-microbial system can further include a secondary preservative or antimicrobial agent. Non-limiting examples of secondary preservatives or antimicrobial agents includes iodopropynyl butylcarbamate, capylyl glycol, imidazolidinyl urea, a paraben (e.g., methylparaben, ethylparaben, propylparaben, etc.) methylsothiazoline, chlorphenesin, or benzoic acid or any combination thereof. A particular combination can include an ester/esters of salicylic acid and glycerin with iodopropynyl butylcarbamate or capylyl glycol or both of iodopropynyl butylcarbamate and capylyl glycol. The amount within the system can be from 10 to 90% or 10 to 50% or from 20 to 30% w/w of caprylyl glycol and from 10 to 90% or 50 to 90% or from 60 to 80% w/w of the ester/esters of salicylic acid and glycerol. In another instance, the preservative or anti-microbial system can include from 0.01 to 10% w/w or 0.1 to 5% w/w or 0.5 to 2% w/w of iodopropynyl butylcarbamate, from 10 to 90% or 10 to 50% or from 20 to 30% w/w of caprylyl glycol and from 10 to 90% or 50 to 90% or from 60 to 80% w/w of the ester/esters of salicylic acid and glycerin. In another instance, the preservative or antimicrobial system can include a combination of the ester/esters of salicylic acid and glycerin and imidazolidinyl urea. Such a preservative or anti-microbial system can include 10 to 90% or 10 to 50% or from 20 to 30% or 20 to 25% of imidazolidinyl urea and 10 to 90% or 50 to 90% or from 60 to 80% or from 70 to 80% w/w of the ester/esters of salicylic acid and glycerin. In other instances, the preservative or anti-microbial system can exclude/not include a secondary preservative or antimicrobial agent. The preservative or anti-microbial systems can be effective in inhibiting the growth of a gram-positive bacteria, a gram-negative bacteria, a yeast or a mold. The gram-positive bacteria can be *Staphyloccus aureus* and/or *Staphylococcus epidermidis*. The gram-negative bacteria can be oxidative gram-gram negative bacteria such as *Pseudomonas aeruginosa, Pseudomonas cepacia*, and/or *Pseudomonas putida*. The gram-negative bacteria can be fermentative gram-negative bacteria. The fermentative gram-negative bacteria can be *Escherichia coli, Klebsiella pneumonia*, and/or *Enterobacter aerogenes*. The yeast can be *Candida albicans*. The mold can be *Aspergillus niger*. The preservative or anti-microbial system can include water or can be anhydrous or substantially anhydrous (i.e., less than 5, 4, 3, 2, or 1 wt % of water). The preservative or anti-microbial systems of the present invention can be included or comprised added to a product formulation such as a cosmetic formulation, a pharmaceutical formulation, a wound care formulation, a wound debridement formulation, a cleansing formulation for skin, a cleansing formulation for hard or inanimate surfaces or objects, a disinfectant formulation for skin, a disinfectant formulation for hard or inanimate surfaces or objects, a food formulation, a shampoo, etc. The formulation in which the preservative or anti-microbial system is added to can be formulated as an emulsion (e.g., water-in-oil, water-in-oil-in-water, oil-in-water, oil-in-water-in-oil, oil-in-water-in-silicone, water-in-silicone, silicone-in-water emulsions), a cream, a lotion, a solution (both aqueous and hydro-alcoholic), an anhydrous base (such as lipsticks and powders), a gel, an ointment, a spray, an aerosol, etc.

Also disclosed is a method of inhibiting the growth of a microorganism comprising contacting the microorganism with any one of the preservative or anti-microbial systems of identified throughout this specification, wherein the growth of the microorganism is inhibited. The microorganism can be a gram-positive bacteria, a gram-negative bacteria, a yeast or a mold. The microorganism can be a gram-positive bacteria, a gram-negative bacteria, a yeast or a mold. The gram-positive bacteria can be *Staphyloccus aureus* and/or *Staphylococcus epidermidis*. The gram-negative bacteria can be oxidative gram-gram negative bacteria such as *Pseudomonas aeruginosa, Pseudomonas cepacia*, and/or *Pseudomonas putida*. The gram-negative bacteria can be fermentative gram-negative bacteria. The fermentative gram-negative bacteria can be

*Escherichia coli, Klebsiella pneumonia*, and/or *Enterobacter aerogenes*. The yeast can be *Candida albicans*. The mold can be *Aspergillus niger*.

In a further embodiment, there is disclosed a method of inhibiting the growth of a microorganism in a formulation comprising adding any one of the preservative or anti-microbial systems disclosed in this specification to said formulation, wherein growth of the microorganism in said formulation is inhibited. The microorganism can be a gram-positive bacteria, a gram-negative bacteria, a yeast or a mold. The microorganism can be a gram-positive bacteria, a gram-negative bacteria, a yeast or a mold. The gram-positive bacteria can be *Staphyloccus aureus* and/or *Staphylococcus epidermidis*. The gram-negative bacteria can be oxidative gram-gram negative bacteria such as *Pseudomonas aeruginosa, Pseudomonas cepacia*, and/or *Pseudomonas putida*. The gram-negative bacteria can be fermentative gram-negative bacteria. The fermentative gram-negative bacteria can be *Escherichia coli, Klebsiella pneumonia*, and/or *Enterobacter aerogenes*. The yeast can be *Candida albicans*. The mold can be *Aspergillus niger*.

In another aspect, there is disclosed a method of inhibiting the growth of a microorganism comprising contacting the microorganism with an imidazolidinyl urea and any one of the preservative or anti-microbial systems of the present invention or any one of the esters of salicylic acid and glycerol of the present invention, wherein the growth of the microorganism is inhibited. The method can include first combining the imidazolidinyl and the preservative or anti-microbial systems of the present invention or any one of the esters of salicylic acid and glycerol of the present invention and then contacting the microorganism. Alternatively, the combination can be placed within a formulation to inhibit growth of the microorganism in said formulation. The microorganism can be a gram-negative bacteria or a mold or both. The gram-negative bacteria can be an oxidative gram-negative bacteria selected from the group consisting of at least *Pseudomonas aeruginosa, Pseudomonas cepacia*, and/or *Pseudomonas putida* and wherein the mold can be *Aspergillus niger*. The method can be defined as a method of increasing the antimicrobial properties of imidazolidinyl urea comprising combining any one of the preservative or anti-microbial systems of the present invention with imidazolidinyl urea, wherein the antimicrobial properties of imidazolidinyl is increased when compared with the antimicrobial properties of imidazolidinyl without the presence of said any one of the preservative or anti-microbial systems of the present invention. As noted above, the increase in antimicrobial properties includes increasing the antimicrobial properties against a gram-negative bacteria or a mold or both. The gram-negative bacteria can be an oxidative gram-negative bacteria selected from the group consisting of at least *Pseudomonas aeruginosa, Pseudomonas cepacia*, and/or *Pseudomonas putida* and wherein the mold can be *Aspergillus niger*.

In still another embodiment, there is disclosed a method of stabilizing an emulsion that includes caprylyl glycol comprising adding any one of the preservative or anti-microbial systems of the present invention to the emulsion, wherein the emulsion is stabilized by the addition of said preservative or anti-microbial systems of the present invention. The amount of said caprylyl glycol in said emulsion can be decreased or increased as needed to inhibit the growth of a microorganism in the emulsion.

The preservative or antimicrobial systems of the present invention can be used in a wide variety of food and drink products. Non-limiting examples of food products include meat, fish, crustaceans, poultry products, bread crumbs, vegetables (including chunks and puree), protein, wheat, sweeteners (including sugar and artificial sweeteners), oil, emulsions, fruit (including chunks and puree), cheese, nuts, spreads (e.g. catsup, mustard, mayonnaise, peanut butter, jelly, etc.). etc. Similarly, these systems can be used in a wide range of topical compositions such as cosmetics or skin care products (e.g., moisturizers, creams, lotions, skin softeners, foundations, night creams, lipsticks, lip gloss, cleansers, toners, sunscreens, masks, anti-aging products, ointments, etc.). Also, the preservative or antimicrobial systems can be used in a wide variety of pharmaceutical products, cleansers, disinfectants, wound care products, wound debridement products, and the like. Further, the formulations can be formulated in a variety of manners (e.g., solutions, creams, lotions, emulsions, ointments, sprays, aerosols, anhydrous systems, sticks (e.g., lipsticks, deodorants), dispersion, etc.).

Also disclosed are the following Embodiments 1 to 41 of the present invention. Embodiment 1 is a preservative or anti-microbial system comprising at least one ester of salicylic acid and glycerin or a salt thereof. Embodiment 2 is the preservative or anti-microbial system of Embodiment 1, wherein the at least one ester of salicylic acid and glycerin has the following formula:

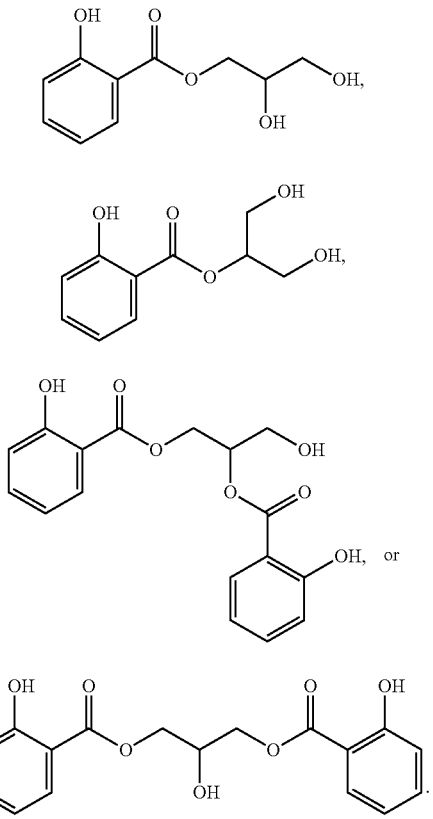

or a salt thereof. Embodiment 3 is the preservative or antimicrobial system of Embodiment 2, comprising at least two, three, or all four of said esters of salicylic acid and glycerin or salts thereof. Embodiment 4 is the preservative or anti-microbial system of Embodiment 3, comprising all four of said esters of salicylic acid and glycerin or salts thereof. Embodiment 5 is the preservative or anti-microbial system of Embodiment 4, comprising:

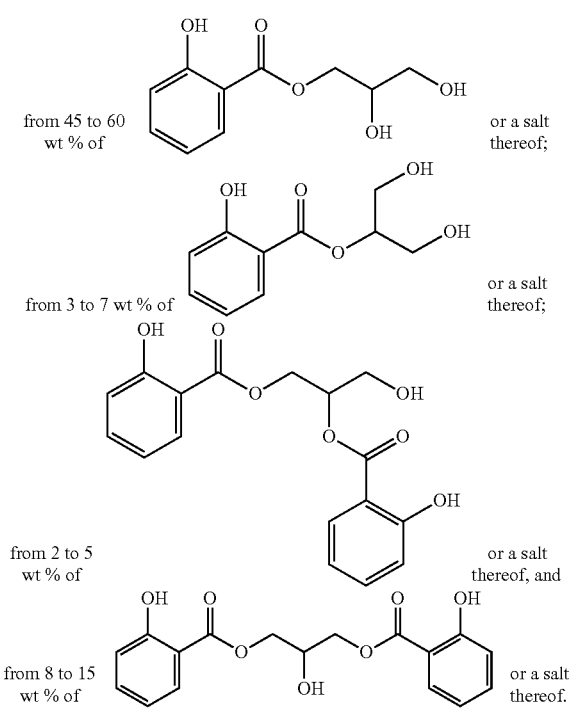

Embodiment 6 is the preservative or anti-microbial system of Embodiment 4, comprising:

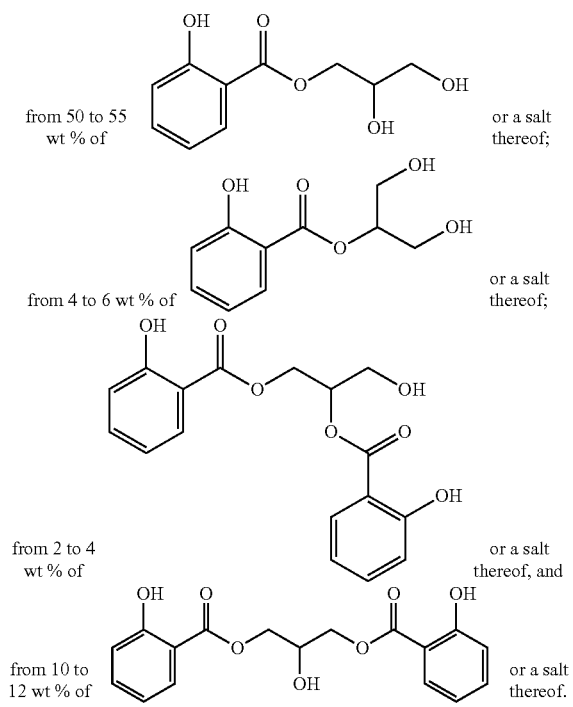

Embodiment 7 is the preservative or anti-microbial system of any one of Embodiments 1 to 6, further comprising glycerin. Embodiment 8 is the preservative or anti-microbial system of Embodiment 7, comprising 15 to 25 wt % of glycerin. Embodiment 9 is the preservative or anti-microbial system of Embodiment 8, comprising 18 to 22 wt % of glycerin. Embodiment 10 is the preservative or anti-microbial system of any one of Embodiments 1 to 9, further comprising a secondary preservative or antimicrobial agent. Embodiment 11 is the preservative or antimicrobial system of Embodiment 10, wherein the secondary preservative or antimicrobial agent is selected from the group consisting of at least one of iodopropynyl butylcarbamate, capylyl glycol, imidazolidinyl urea, a paraben, methylsothiazoline, chlorphenesin, or benzoic acid or any combination thereof. Embodiment 12 is the preservative or antimicrobial system of Embodiment 11, comprising iodopropynyl butylcarbamate or capylyl glycol or both of iodopropynyl butylcarbamate and capylyl glycol. Embodiment 13 is the preservative or anti-microbial system of Embodiment 12, comprising: from 20 to 25% w/w of caprylyl glycol; and from 70 to 80% w/w of the ester/esters of salicylic acid and glycerin. Embodiment 14 is the preservative or anti-microbial system of Embodiment 13, comprising: from 0.5 to 2% w/w of iodopropynyl butylcarbamate; from 20 to 25% w/w of caprylyl glycol; and from 70 to 80% w/w of the ester/esters of salicylic acid and glycerin. Embodiment 15 is the preservative or antimicrobial system of Embodiment 11, comprising imidazolidinyl urea. Embodiment 16 is the preservative or anti-microbial system of Embodiment 15, comprising: from 20 to 25% w/w of imidazolidinyl urea; and from 70 to 80% w/w of the ester/esters of salicylic acid and glycerin. Embodiment 17 is the preservative or anti-microbial system of any one of Embodiments 1-16, wherein said system is effective in inhibiting the growth of a gram-positive bacteria, a gram-negative bacteria, a yeast or a mold. Embodiment 18 is the preservative or anti-microbial system of Embodiment 17, wherein the gram-positive bacteria is Staphyloccus aureus and/or Staphylococcus epidermidis, wherein the gram-negative bacteria is oxidative gram-gram negative bacteria selected from the group consisting of at least one of Pseudomonas aeruginosa, Pseudomonas cepacia, and/or Pseudomonas putida, wherein the gram-negative bacteria is fermentative gram-negative bacteria selected from the group consisting of Escherichia coli, Klebsiella pneumonia, and/or Enterobacter aerogenes, wherein the yeast is Candida albicans, and wherein the mold is Aspergillus niger. Embodiment 19 is the preservative or anti-microbial system of any one of Embodiments 1 to 18, wherein said system is substantially anhydrous. Embodiment 20 is the preservative or anti-microbial system of any one of Embodiments 1 to 19, wherein said system does not include salicylic acid and/or does not include a paraben. Embodiment 21 is the preservative or anti-microbial system of any one of Embodiments 1 to 20, wherein said system is comprised within a cosmetic formulation or a pharmaceutical formulation. Embodiment 22 is the preservative or anti-microbial system of Embodiment 21, wherein said formulation is an emulsion, solution, or ointment. Embodiment 23 is the preservative or anti-microbial system of any one of Embodiments 1 to 20, wherein said system is a disinfectant formulation or a cleansing formulation. Embodiment 24 is the preservative or anti-microbial system of any one of Embodiments 21 to 23, wherein said formulation comprises from 0.1 to 10 wt. % or 0.5 to 5 wt. % or 1 to 3 wt. % of any one of said preservative or anti-microbial systems. Embodiment 25 is a method of inhibiting the growth of a microorganism comprising contacting the microorganism with any one of the preservative or anti-microbial systems of Embodiments 1 to 24, wherein the growth of the microorganism is inhibited. Embodiment 26 is the method of Embodiment 25, wherein the microorganism is a gram-positive bacteria, a gram-negative bacteria, a yeast or a mold. Embodiment 27 is the method of Embodiment 26, wherein the gram-positive bacteria is Staphyloccus aureus and/or Staphylococcus epidermidis, wherein the gram-negative bacteria is oxidative gram-gram negative bacteria selected from the group consisting of at least one of *Pseudomonas aeruginosa*, *Pseudomonas cepacia*, and/or *Pseudomonas putida*, wherein the gram-negative bacteria is fermentative gram-negative bacteria selected from the group consisting of *Escherichia coli*, *Klebsiella pneumonia*, and/or *Enterobacter aerogenes*, wherein the yeast is *Candida albicans*, and wherein the mold is *Aspergillus niger*. Embodiment 28 is a method of inhibiting the growth of a microorganism in a cosmetic or pharmaceutical formulation comprising adding any one of the preservative or anti-microbial systems of Embodiments 1 to 24 to said formulation, wherein growth of the microorganism in said formulation is inhibited. Embodiment 29 is the method of Embodiment 28, wherein the microorganism is a gram-positive bacteria, a gram-negative bacteria, a yeast or a mold. Embodiment 30 is the method of Embodiment 29, wherein the gram-positive bacteria is *Staphyloccus aureus* and/or *Staphylococcus epidermidis*, wherein the gram-negative bacteria is oxidative gram-gram negative bacteria selected from the group consisting of at least one of *Pseudomonas aeruginosa*, *Pseudomonas cepacia*, and/or *Pseudomonas putida*, wherein the gram-negative bacteria is fermentative gram-negative bacteria selected from the group consisting of *Escherichia coli*, *Klebsiella pneumonia*, and/or *Enterobacter aerogenes*, wherein the yeast is *Candida albicans*, and wherein the mold is *Aspergillus niger*. Embodiment 31 is a method of inhibiting the growth of a microorganism comprising contacting the microorganism with an imidazolidinyl urea and any one of the preservative or anti-microbial systems of Embodiments 1 to 24, wherein the growth of the microorganism is inhibited. Embodiment 32 is the method of Embodiment 31, wherein the microorganism is a gram-negative bacteria or a mold or both. Embodiment 33 is the method of Embodiment 32, wherein the gram-negative bacteria is an oxidative gram-negative bacteria selected from the group consisting of at least *Pseudomonas aeruginosa*, *Pseudomonas cepacia*, and/or *Pseudomonas putida* and wherein the mold is *Aspergillus niger*. Embodiment 34 is a method of inhibiting the growth of a microorganism in a cosmetic or pharmaceutical formulation comprising adding an imidazolidinyl urea and any one of the preservative or anti-microbial systems of Embodiments 1 to 24 to the formulation, wherein growth of the microorganism in the formulation is inhibited. Embodiment 35 is the method of Embodiment 34, wherein the microorganism is a gram-negative bacteria or a mold or both. Embodiment 36 is the method of Embodiment 35, wherein the gram-negative bacteria is an oxidative gram-negative bacteria selected from the group consisting of at least *Pseudomonas aeruginosa*, *Pseudomonas cepacia*, and/or *Pseudomonas putida* and wherein the mold is *Aspergillus niger*. Embodiment 37 is a method of increasing the antimicrobial properties of imidazolidinyl urea comprising combining any one of the preservative or anti-microbial systems of Embodiments 1 to 24 with imidazolidinyl urea, wherein the antimicrobial properties of imidazolidinyl are increased when compared with the antimicrobial properties of imidazolidinyl without the presence of said any one of the preservative or anti-microbial systems of Embodiments 1 to 24. Embodiment 38 is the method of Embodiment 37, wherein the increase in antimicrobial properties includes increasing the antimicrobial properties against a gram-negative bacteria or a mold or both. Embodiment 39 is the method of Embodiment 38, wherein the gram-negative bacteria is an oxidative gram-negative bacteria selected from the group consisting of at least *Pseudomonas aeruginosa*, *Pseudomonas cepacia*, and/or *Pseudomonas putida* and wherein the mold is *Aspergillus niger*. Embodiment 40 is a method of stabilizing an emulsion that includes caprylyl glycol comprising adding any one of the preservative or anti-microbial systems of Embodiments 1 to 24 to the emulsion, wherein the emulsion is stabilized by the addition of said preservative or anti-microbial system. Embodiment 41 is the method of Embodiment 40, wherein the amount of said caprylyl glycol in said emulsion is decreased or increased as needed to inhibit the growth of a microorganism in the emulsion.

It is contemplated that any embodiment discussed in this specification can be implemented with respect to any method or composition of the invention, and vice versa. Furthermore, compositions of the invention can be used to achieve methods of the invention.

The term "about" or "approximately" are defined as being close to as understood by one of ordinary skill in the art, and in one non-limiting embodiment the terms are defined to be within 10%, within 5%, within 1%, and/or within 0.5%.

The terms "inhibiting" or "reducing" or "retarding" or "preventing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The term "preservation" refers to the prevention or retardation or reduction or inhibition of product deterioration due to microorganisms present in the product. A "preservative or antimicrobial system" is an ingredient or mixture of ingredients that is effective in preventing, retarding, reducing, or inhibiting the growth of microorganisms in a product or formulation (e.g., pharmaceutical or cosmetic formulation).

The "at least one ester of salicylic acid and glycerol" includes at least one, two, three, or all four of 1 glycerol mono-salicylate, 2 glyceryl mono-salicylate, 1,2 glyceryl di-salicylate, and/or 1,3 glycerol di-salicylate, and/or salt forms and derivatives thereof.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The preservative or antimicrobial systems of the present invention can "comprise," "consist essentially of," or "consist of" particular method steps, ingredients, components, compositions, etc. disclosed throughout the specification. With respect to the transitional phase "consisting essentially of," in one non-limiting aspect the basic and novel characteristic of the preservative or antimicrobial systems are their preservative or antimicrobial properties.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Figure 1:
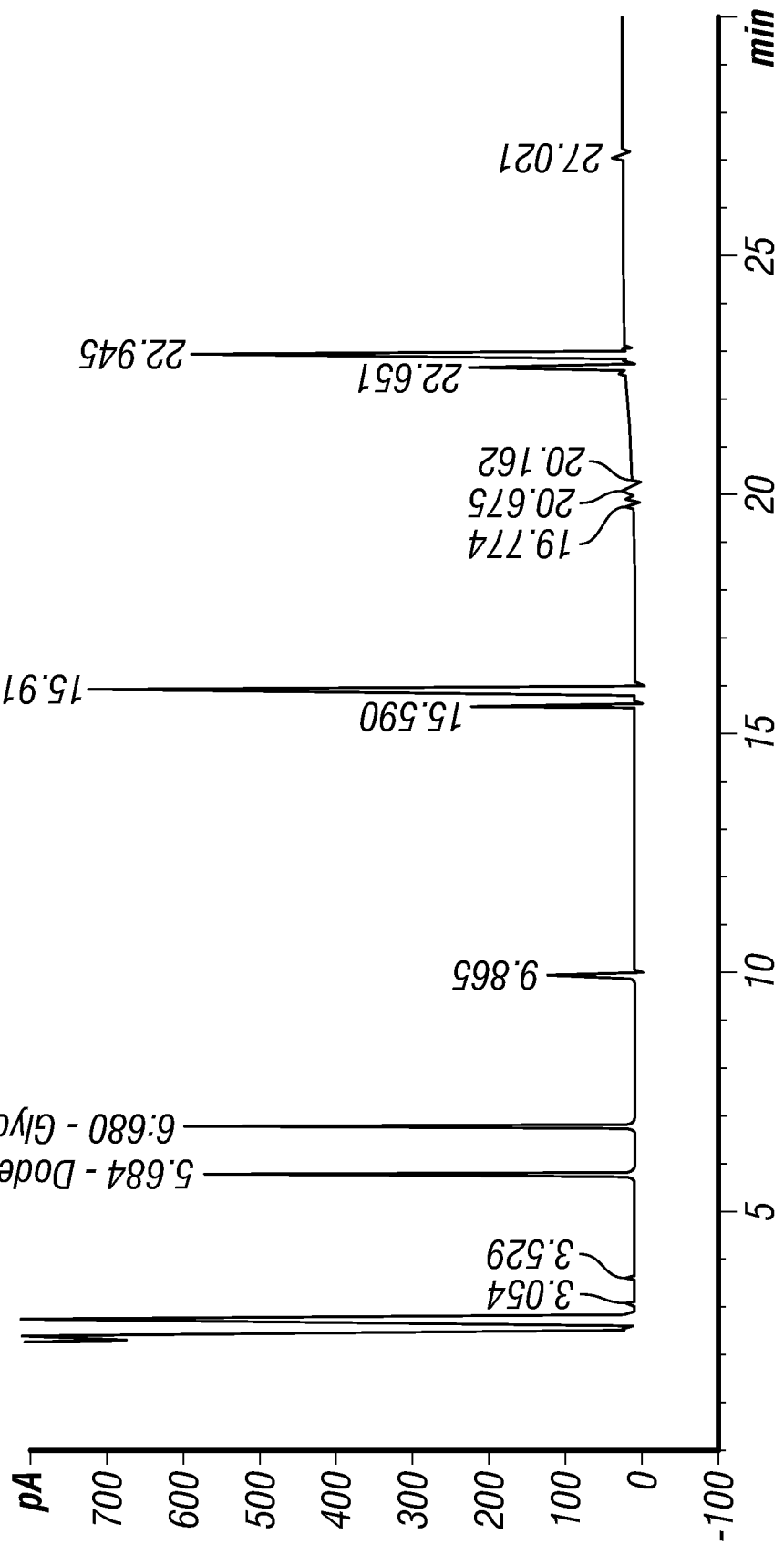
FIG. 1: GC-FID Chromatogram for a glycerol salicylate sample.

Preservatives or antimicrobials are widely used in the cosmetics, pharmaceuticals, foods, cleansing, and disinfecting industries. As noted above, there are a wide range of known preservatives/antimicrobials. Many of these ingredients can be caustic to skin, be difficult to formulate with, and require multiple combinations of ingredients to achieve broad spectrum protection against microorganism growth within a given formulation.

One of the current problems associated with preserving a given formulation is that preservatives remain necessary to prevent microbial contamination. There are a limited number of potential options as of today, many of which are caustic or skin irritating and are difficult to formulate with.

A solution is presented to the current problems facing current preservative or antimicrobial systems. The solution is based on a mixture of esters of salicylic acid with glycerol (or combination of said esters) that has excellent antimicrobial properties. Without wishing to be bound by theory, it is believed that the glycerol portion of the esters of the present invention can hydrogen bond with the hydrophilic surface of the microorganism cell membrane (e.g., the phosphor end of the phospholipids) while the more hydrophobic end of the salicylic acid molecule inserts itself into the hydrophobic region of cell membrane (e.g., lipid end of the phospholipid), thereby disrupting the cell wall of the microorganism. Also, the esters of the present invention can attach to proteins or other functionalities on the cell membrane and cause a given protein or enzyme to shut down.

These and other non-limiting aspects of the present invention are provided in the following subsection.

A. Esters of Salicylic Acid and Glycerol

A glycerol (glycerin) has the following structure:

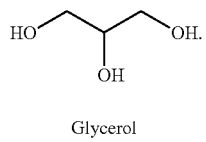

Glycerol

Salicylic acid has the following structure:

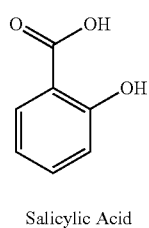

Salicylic Acid

Esters of salicylic acid and glycerol that can be used in the preservative or antimicrobial systems of the present invention include any one of, any combination of, or all of the following:

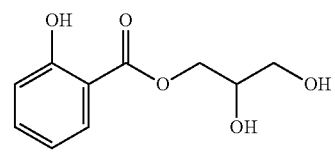

1 glyceryl mono-salicylate

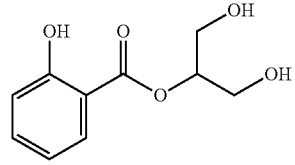

2 glyceryl mono-salicylate

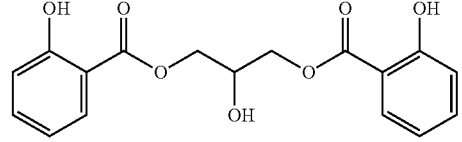

1,3 glyceryl di-salicylate

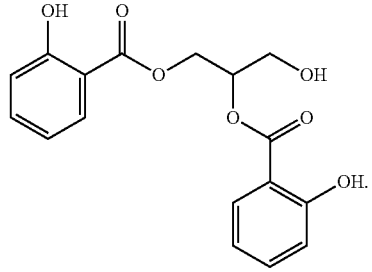

1,2 glycerol di-salicylate

Further, the amounts of each of the above esters within a mixture can vary as desired. For example, the mixture can include 30 to 60 wt % of 1 glyceryl mono-salicylate, 1 to 5 wt % of 2 glyceryl mono-salicylate, 1 to 6 wt % of 1,2 glyceryl di-salicylate, and 10 to 25 wt % of 1,3 glyceryl di-salicylate. Further, the mixture can also include glycerin at amounts ranging from 10 to 25 wt % and/or salicylic acid at amounts ranging from 1 to 6 wt %. The mixtures can be used in a formulation as a preservative or antimicrobial system in amounts ranging from 0.01 to 10 wt % or from 0.1 to 5 wt % or from 1 to 3 wt % or as needed to preserve a given formulation.

Additionally, salt forms of the above esters can be used in the context of the present invention. Further, the above esters can be modified or derivatized as desired. For instance, free OH groups can each independently be replaced with an H, an acid molecule, a hydroxy, a halogen, an oxo (e.g., ether), an alkoxy, a silyloxy, an acyl, an aryl, an acetyl, a carbonyl, a cyano, a heterocyclyl, an amido, an aminocarbonyl, an amino, —NH-alkyl, —N(alkyl)$_2$, —NH-(substituted alkyl), —N-(substituted alkyl)$_2$, —NH-aryl, —N(aryl)$_2$, an azido, a trialkylsilyloxy, an acyloxy, a acylamino, a bis-acylamino, an ester, a NO, a NO$_2$, or a sulfo (e.g., thioether, thioester, thiocarbonyl, sulfonamido, sulfonyl, etc.). The free OH groups can also each independently be replaced with alkyl groups, carboxyl groups, carbonyl groups, nitro groups, amino groups, amide groups, azo groups, sulfate groups, sulfonate groups, sulfono groups, sulfhydryl groups, sulfonyl groups, sulfoxido groups, phosphate groups, phosphors groups, phosphoryl groups, and/or halide groups. The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The term "alkoxy" includes a group having the structure —OR, where R is an alkyl group. Non-limiting examples of alkoxy groups include —OCH$_3$, —OCH$_2$CH$_3$, —OCH$_2$CH$_2$CH$_3$, —OCH(CH$_3$)$_2$, —OCH(CH$_2$)$_2$, etc. The term "hydroxyalkyl" includes an alkyl group having at least one hydroxy group.

B. Obtaining the Esters of Salicylic Acid and Glycerol

The glycerol salicylate mixtures used in the examples were prepared and provided by Alzo International Inc. (New Jersey, USA).

Additionally, the esters of salicylic acid and glycerol can be prepared by using convention chemical synthesis techniques (see, e.g., Organic Chemistry, 5$^{th}$ Ed.). In one instance, a standard transesterification process can be used in which methyl salicylate and glycerin can be reacted in sufficient amounts in the presence of a base such as sodium methoxide. Once the reaction is completed, any unwanted materials can be removed. For instance, methyl salicylate, glycerin, salicylic acid, impurities, etc. can be removed through various purification steps ranging from steam distillation, column chromatography, lyophilization, etc. Further, if a particular ester of salicylic acid and glycerol is desired over another, then particular esters can be isolated and used in the context of the present invention. Such isolation steps are known to those of ordinary skill in the art.

An additional esterification method that can be used includes the Fisher-Speier Esterification process. This process is performed by refluxing a carboxylic acid (i.e., salicylic acid) and an alcohol (i.e., glycerol) in the presence of an acid catalyst. Commonly used catalysts include sulfuric acid, tosic acid, and Lewis acids such as scandium(III) triflate. The reaction can be performed without using a solvent (particularly when a large reagent excess (e.g., of MeOH is used) or in a non-polar solvent (e.g., toluene) to facilitate the Dean-Stark method. Typical reaction times vary from 1-10 hours at temperatures of 60-110° C. A generic mechanism for this type of reaction is provided below:

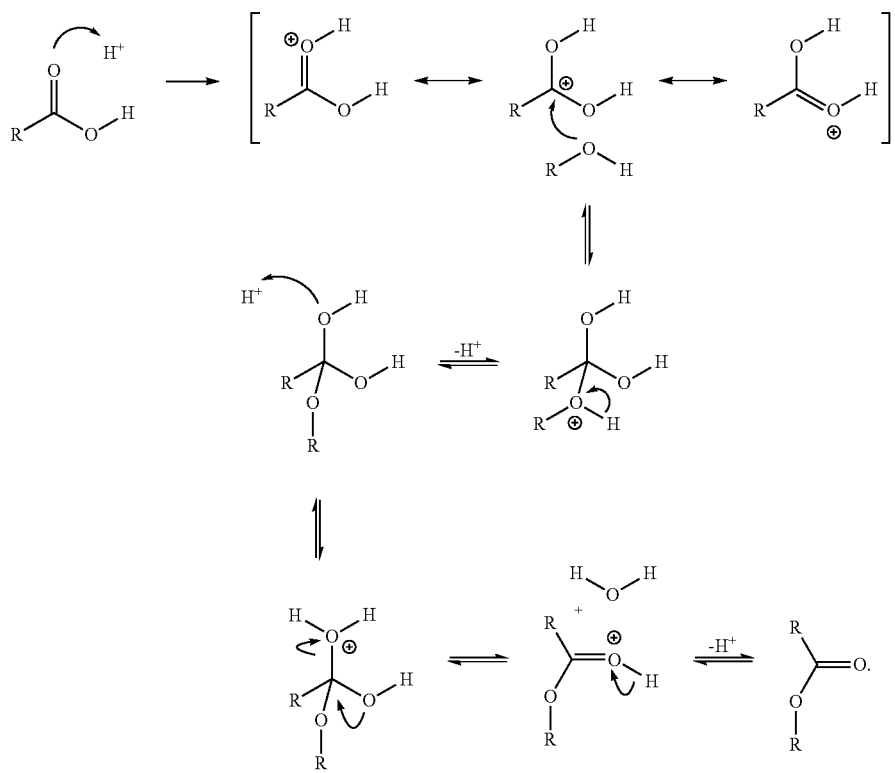

C Vehicles/Formulations

The preservative or anti-microbial systems of the present invention can be incorporated into all types of vehicles. Non-limiting examples of suitable vehicles include emulsions (e.g., water-in-oil, water-in-oil-in-water, oil-in-water, oil-in-water-in-oil, oil-in-water-in-silicone, water-in-silicone, silicone-in-water emulsions), creams, lotions, solutions (both aqueous and hydro-alcoholic), anhydrous bases (such as lipsticks and powders), gels, ointments, sprays, aerosols, etc. and other known to one of ordinary skill in the art (see, e.g., Remington's, 1990 and International Cosmetic Ingredient Dictionary and Handbook, 10$^{th}$ Ed., 2004)).

Further, the vehicles/formulations can include a wide range of additional ingredients. Examples of cosmetic ingredients include those listed in the CTFA International Cosmetic Ingredient Dictionary and Handbook (2008). Some non-limiting specific examples include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

Examples pharmaceutical ingredients that can be included in the vehicles/formulations of the present invention include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

D Kits

Kits are also contemplated as being used in certain aspects of the present invention. For instance, the preservative or anti-microbial systems of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

EXAMPLES

The following examples are included to demonstrate certain non-limiting aspects of the invention. It should be appreciated by those of skill in the art that the techniques disclosed in the examples which follow representative techniques discovered by the inventor to function well in the practice of the invention. However, those of skill in the art should appreciate that changes can be made in the specific embodiments which are disclosed and still obtain a like or similar result without departing from the spirit and scope of the invention.

Example 1

Characterization of the Glycerol Salicylate Antimicrobial System

Figure 2:
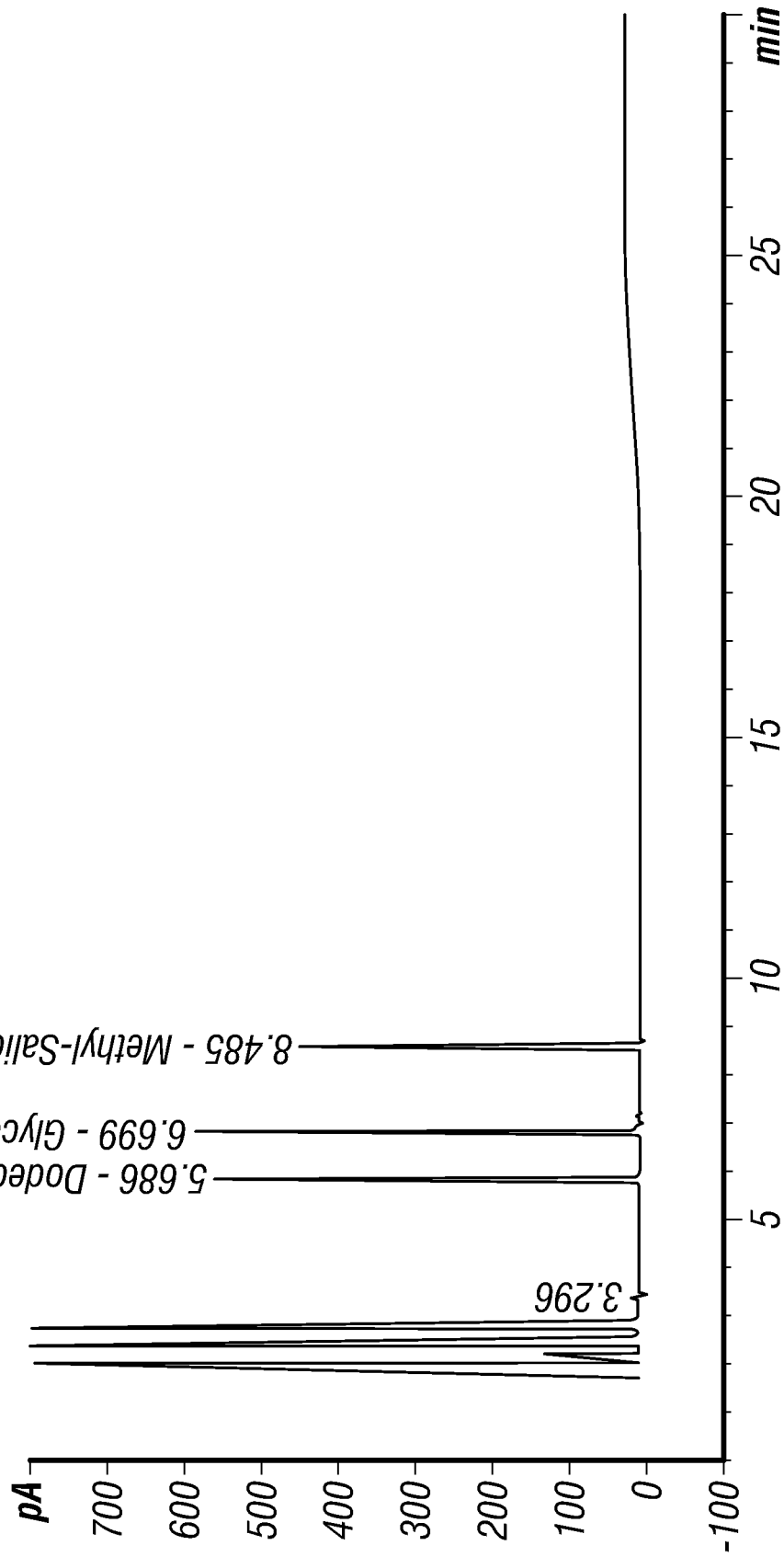
FIG. 2: GC-FID Chromatogram for a glycerol salicylate sample.

The glycerol salicylate antimicrobial system having the aforementioned glycerol salicylate compounds was prepared by using a standard transesterification process in which methyl salicylate and glycerin were reacted in the presence of a base (i.e., sodium methoxide). After the reaction is completed, any unreacted methyl salicylate is removed through steam distillation and citric acid is used to neutralize the base. Various samples of glycerol salicylate were prepared by Alzo International Inc. (New Jersey, USA) using this method. These samples were also used to procure the following data. Table 1 provides data on various glycerol salicylate samples that were characterized using GC-FID using dodecane as the internal standard. FIGS. 1 and 2 are GC-FID Chromatograms for various glycerol salicylate samples.

TABLE 1*

| ID (RT) | Glycerol (6.7 min) | Methyl Salicylate (8.5 min) | MS Isomer (9.9 min) | Glycerol Salicylate M-2 (15.6 min) | Glycerol Salicylate M-1 (15.9 min) | unknown (20.1 min) | Glycerol Salicylate D-1,2 (22.7 min) | Glycerol Salicylate D-1,3 (23.0 min) | unknown (27.0 min) | Everything Total | Glycerol Salicylate total* |
|---|---|---|---|---|---|---|---|---|---|---|---|
| Lot#: 184-175 (007-06B) #1 | 15.01747 | | 2.16614 | 4.67121 | 57.76431 | 0.80519 | 5.50029 | 19.20900 | 0.53035 | 105.66 | 84.98 |
| 184-175 #2 | 14.72046 | | 2.15493 | 4.64515 | 57.43445 | 0.73549 | 5.57512 | 18.87364 | 0.51770 | 104.66 | 85.28 |
| Lot#: 183-207 (007-06) #1 | 15.82275 | | 2.73317 | 1.76257 | 57.15688 | 0.73810 | 0.98152 | 21.92985 | 0.48670 | 101.61 | 84.18 |
| 183-207 #2 | 15.72048 | | 2.76593 | 1.84238 | 59.31755 | 0.77354 | 1.03425 | 23.23140 | 0.51480 | 105.20 | 84.28 |
| Lot#: 184-9b #1 | 17.15233 | 8.55084 | 1.90066 | 4.38084 | 54.13868 | 0.59753 | 4.41621 | 15.54202 | 0.36950 | 107.05 | 74.30 |
| Lot#: 184-9b #2 | 16.77172 | 8.22224 | 1.83444 | 4.13057 | 51.05724 | 0.56156 | 4.24099 | 14.80689 | 0.35457 | 101.98 | 75.01 |
| Lot#: 184-9c #1 | 17.79987 | | 2.32601 | 4.77400 | 57.34256 | 0.67816 | 4.56697 | 16.99760 | 0.39528 | 104.88 | 82.20 |
| Lot#: 184-9c #1 | 18.00305 | | 2.34642 | 4.82604 | 57.95203 | 0.69427 | 4.73990 | 17.60363 | 0.41587 | 106.58 | 82.00 |

*Glycerol Salicylate Total is calculated by 100%-Glycerin %-Methyl Salicylate % since Glycerin and Methyl Salicylate percentages are accurate.

Additional samples were further tested and related data is provided in Table 2. MC0000000106944 is a large scale production scale sample, whereas 175-211 is a lab scale sample:

TABLE 2

| TEST NAME | TEST RESULT MC0000000106944 | TEST RESULT 175-211 |
|---|---|---|
| Appearance | clear, viscous liquid, over time the appearance becomes more hazy with particles settling to the bottom of the container | Initially liquid, solidified to white particles |
| Color | pale amber | off white when solid, clear amber when liquid |
| Odor | faint | faint |
| Acid Value | 1.30 | 0.53 |
| SAP Value | 212.60 | 221.20 |
| IR Scan | completed | — |
| Nitrites | none detected | — |
| pH | 6.53 | 6.62 |
| Refractive Index | 1.5429 | — |
| Citric Acid | 0.04 | 0.00 (none detected) |
| Gardner Color | <1 | — |
| Glycerin | 20.21 | 17.14 |
| Glycolic Acid | 0.29 | 0.33 |
| Glycerol Sal M-1 | 39.85 | 39.43 |
| Glycerol Sal M-2 | 3.48 | 1.28 |
| Glycerol Sal D-1,2 | 5.35 | 0.82 |
| Glycerol Sal Di-1,3 | 16.37 | 24.66 |
| Glycerol Tri-Sal | 1.38 | 2.28 |
| Glycerol Salicylate Total by HPLC | 66.43 | 68.47 |
| Glycerol Sal M-1 | 53.72 | 53.58 |
| Glycerol Sal M-2 | 4.60 | 1.28 |
| Glycerol Sal Di-1,2 | 3.32 | 0.47 |
| Glycerol Sal Di-1,3 | 11.22 | 17.43 |
| Glycerol Tri-Sal | 0.00 | 0.0 |
| Glycerol Salicylate Total by GC | 72.85 | 72.05 |
| Loss on Drying | — | 2.15 |
| Loss on Ignition | — | 99.55 |
| Methyl Salicylate | 0.00 | 0.0 |
| Salicylic Acid | 5.408 | 2.810 |

Example 2

Antimicrobial Data

A proprietary base lotion formulation having no preservatives ("Vinny Base") was used as a control. Three separate preservative systems were each added to the Vinny Base, thereby creating four total formulations. The first formulation was the Vinny Base. The second formulation was the Vinny Base+1 wt % of the glycerol salicylate from Example 1 (the large scale production sample MC0000000106944 was used). The third formulation was the Vinny Base+0.3 wt % of Germall® 115 (Imidazolidinyl Urea) (can be purchased from Ashland Inc. (Covington, Ky., USA), a known preservative. The fourth formulation was the Vinny Base+0.3 wt % of Germall® 115+1% of the glycerol salicylate from Example 1 (the large scale production sample MC0000000106944 was used). Each of the four formulations were initially inoculated with each group of the following bacteria at a concentration of 100,000 ($10^5$) to 1,000,000 ($10^6$) organisms/gram of product and the following yeast and mold at a concentration of 10,000 ($10^4$) to 100,000 ($10^5$) organisms/gram of product:
  (1) Gram-positive bacteria from *Staphylococcus aureus* and *Staphylococcus epidermis*.
  (2) Fermentative gram-negative bacteria from *Escherichia coli*, *Klebsiella pneumonia*, and *Enterobacter aerogenes*.
  (3) Oxidative gram-negative bacteria from *Pseudomonas aeruginosa*, *Pseudomonas cepacia*, and *Pseudomonas putida*.
  (4) Yeast from *Candida albicans*.
  (5) Mold from *Aspergillus niger*.

Five (5) to seven (7) days after initial inoculation, each of the four formulations were tested to determine the amount of microorganism growth that survives in formulations. This was considered the week one (1) read. If the product showed growth at the week 1 read, then it is was retested after an additional five (5) to seven (7) days, which was considered the week two (2) read. If the product showed growth at the week 2 read, then it is was retested after an additional five (5) to seven (7) days, which was considered the week three (3) read. If the product showed growth at the week three (3) read, then it is was retested after an additional five (5) to seven (7) days, which was considered the week four (4) read. The testing parameters generally followed the USP 51 Antimicrobial Effectiveness Test or "Challenge Testing" pursuant to chapter 51 of the United States Pharmacopeia (USP); although additional microorganism were tested to further confirm the effectiveness of the glycerol salicylate preservative system. A summary of the USP 51 Antimicrobial Effectiveness Test is provided below:
  (1) USP 51 challenges (inoculates) a formula with 5 different microorganisms, separately. Three bacteria and two fungal strains are used for each USP 51 test.
  (2) Test microorganisms are grown in liquid or on solid medium, depending on the microorganism.
  (3) Microorganisms used for a USP 51 test follow:
    *Candida albicans* (a yeast . . . yeasts are a form of fungus)
    *Aspergillus brasiliensis* (a filamentous mold . . . also a fungus)

*Escherichia coli* (a bacterium . . . better known as "*E. coli*")

*Pseudomonas aeruginosa* (a bacterium . . . very problematic industrially)

*Staphylococcus aureus* (a bacterium . . . better known as "Staph")

(4) The test microorganisms are either harvested by centrifugation from broth culture or by washing surface growth from a solid medium into a sterile vessel.

(5) The concentrations of test microorganisms are standardized by resuspending harvested microorganisms in sterile saline to yield $\sim 1 \times 10^8$ CFU/ml.

(6) A recovery analysis is performed to verify that microorganisms present in a sample can be adequately recovered and enumerated using the chosen dilution and plating scheme.

(7) A sufficient volume of test product (typically 10 ml) is distributed into each of 5 separate containers, and each container is inoculated with a separate test microorganism (mentioned above).

(8) The initial concentration of viable microorganisms in the test product is determined by standard dilution and plate count methods.

(9) Inoculated test products are incubated at 22.5±2.5° C. and sampled to determine microorganism concentration at 7, 14 and/or 28 day intervals depending on the product category into which the formulation falls.

(10) The microorganism concentration at each interval is compared to the initial concentration, and then preservative effectiveness is determined based USP guidelines.

Testing on the first formulation (Vinny Base with no preservatives) showed that the formulation is vulnerable to all of the tested microorganisms at weeks 1 to 4—microorganism growth was present.

Testing on the second formulation (Vinny Base+1 wt % of the glycerol salicylate from Example 1) showed that at week 1, the formulation showed vulnerability for oxidative gram-negatives and mold. At week 2, the formulation showed the same vulnerability as week 1. At week 3, the formulation showed vulnerability for oxidative gram negatives and yeast. At week 4, the formulation showed the same vulnerability as week 3.

Testing on the third formulation (Vinny Base+0.3 wt % of Germall® 115 (Imidazolidinyl Urea)) showed that at week 1, the formulation showed vulnerability for fermentative gram-negative bacteria, oxidative gram-negative bacteria, yeast and mold. At week 2, the formulation showed vulnerability for oxidative gram-negative bacteria, yeast and mold. At week 3, the formulation showed vulnerability for yeast and mold. At week 4, the formulation showed the same vulnerability as week 3.

Testing on the fourth formulation (Vinny Base+0.3 wt % of Germall® 115+1% of the glycerol salicylate from Example 1) showed that at week 1, the formulation did not show any vulnerability for any of the tested microorganisms. This is a synergistic outcome, as the week 1 testing for the second formulation (Vinny Base+1 wt % of the glycerol salicylate from Example 1) and the third formulation (Vinny Base+0.3 wt % of Germall® 115 (Imidazolidinyl Urea)) each showed vulnerability for oxidative gram-negative bacteria and mold. However, when both the glycerol salicylate and imidazolidinyl urea preservatives were combined together in the Vinny Base, there was no vulnerability to either of the oxidative gram-negative bacteria and mold. The combination of glycerol salicylate and imidazolidinyl urea provided an unexpected boost of performance against oxidative gram-negative bacteria and mold. No further testing was performed on the fourth formulation due to the fact that no growth was seen after the week 1 test.

A summary of the above data is provided in Tables 3-6.

TABLE 3*

(week 1)

| Week 1 | No Preservatives (formulation 1) | 1% Glycerol Salicylate (formulation 2) | 0.3% Germall ® 115 (formulation 3) | 1% Glycerol Salicylate + 0.3% Germall ® 115 (formulation 4) |
| --- | --- | --- | --- | --- |
| Gram (+) Bacteria | Growth | Minimal Growth/No Growth | Minimal Growth/No Growth | Minimal Growth/No Growth |
| Fermentative Gram (−) Bacteria | Growth | Minimal Growth/No Growth | Growth | Minimal Growth/No Growth |
| Oxidative Gram (−) Bacteria | Growth | Growth | Growth | Minimal Growth/No Growth |
| Yeast | Growth | Minimal Growth/No Growth | Growth | Minimal Growth/No Growth |
| Mold | Growth | Growth | Growth | Minimal Growth/No Growth |

*Minimal growth/no growth is defined as 0-100 cfu/g. Such level of growth is not considered significant in cosmetic or pharmaceutical formulations.

TABLE 4*

| Week 2 | No Preservatives (formulation 1) | 1% Glycerol Salicylate (formulation 2) | 0.3% Germall ® 115 (formulation 3) | 1% Glycerol Salicylate + 0.3% Germall ® 115 (formulation 4) |
|---|---|---|---|---|
| Gram (+) Bacteria | Growth | Minimal Growth/No Growth | Minimal Growth/No Growth | No test |
| Fermentative Gram (−) Bacteria | Growth | Minimal Growth/No Growth | Minimal Growth/No Growth | No test |
| Oxidative Gram (−) Bacteria | Growth | Growth | Growth | No test |
| Yeast | Growth | Minimal Growth/No Growth | Growth | No test |
| Mold | Growth | Growth | Growth | No test |

*Minimal growth/no growth is defined as 0-100 cfu/g. Such level of growth is not considered significant in cosmetic or pharmaceutical formulations.

TABLE 5*

(week 3)

| Week 3 | No Preservatives (formulation 1) | 1% Glycerol Salicylate (formulation 2) | 0.3% Germall ® 115 (formulation 3) | 1% Glycerol Salicylate + 0.3% Germall ® 115 (formulation 4) |
|---|---|---|---|---|
| Gram (+) Bacteria | Growth | Minimal Growth/No Growth | Minimal Growth/No Growth | No test |
| Fermentative Gram (−) Bacteria | Growth | Minimal Growth/No Growth | Minimal Growth/No Growth | No test |
| Oxidative Gram (−) Bacteria | Growth | Growth | Minimal Growth/No Growth | No test |
| Yeast | Growth | Growth | Growth | No test |
| Mold | Growth | Minimal Growth/No Growth | Growth | No test |

*Minimal growth/no growth is defined as 0-100 cfu/g. Such level of growth is not considered significant in cosmetic or pharmaceutical formulations.

TABLE 6*

(week 4)

| Week 4 | No Preservatives (formulation 1) | 1% Glycerol Salicylate (formulation 2) | 0.3% Germall ® 115 (formulation 3) | 1% Glycerol Salicylate + 0.3% Germall ® 115 (formulation 4) |
|---|---|---|---|---|
| Gram (+) Bacteria | Growth | Minimal Growth/No Growth | Minimal Growth/No Growth | No test |
| Fermentative Gram (−) Bacteria | Growth | Minimal Growth/No Growth | Minimal Growth/No Growth | No test |
| Oxidative Gram (−) Bacteria | Growth | Growth | Minimal Growth/No Growth | No test |
| Yeast | Growth | Growth | Growth | No test |
| Mold | Growth | Minimal Growth/No Growth | Growth | No test |

*Minimal growth/no growth is defined as 0-100 cfu/g. Such level of growth is not considered significant in cosmetic or pharmaceutical formulations.

All of the compounds, compositions, and/or methods disclosed and claimed can be made and executed without undue experimentation in light of the present disclosure. While the compounds, compositions, and methods of this invention have been described in terms of certain embodiments, it will be apparent to those of skill in the art that variations may be applied to the compounds, compositions, and/or methods and in the steps or in the sequence of steps of the method without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

The invention claimed is:

1. A preservative or anti-microbial system comprising an effective amount of at least three of the following esters of salicylic acid and glycerin or salts thereof for inhibiting growth of a microorganism:

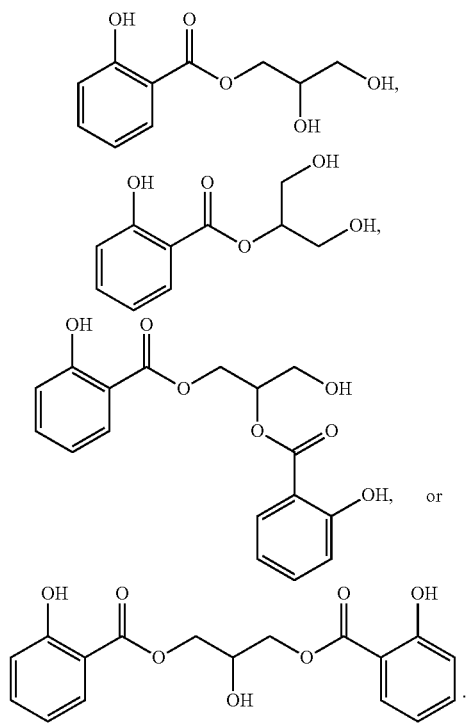

2. The preservative or anti-microbial system of claim 1, comprising all four of said esters of salicylic acid and glycerin or salts thereof.

3. The preservative or anti-microbial system of claim 2, comprising:

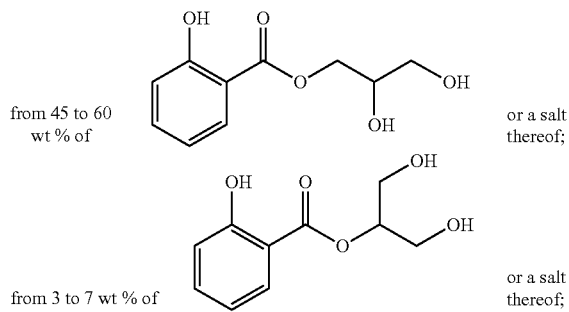

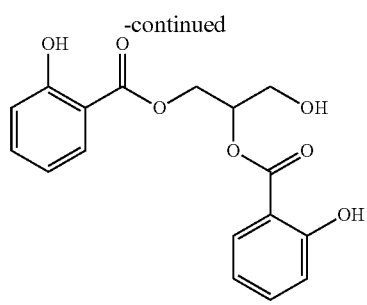

4. The preservative or anti-microbial system of claim 2, comprising:

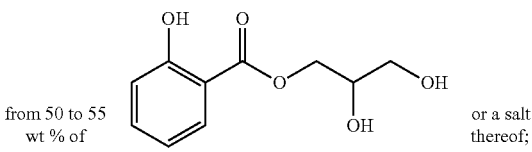
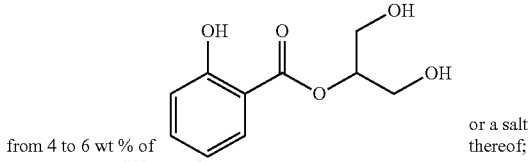
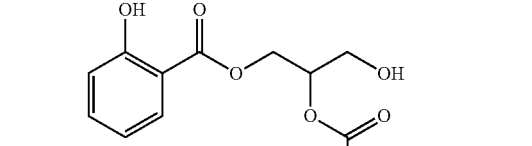
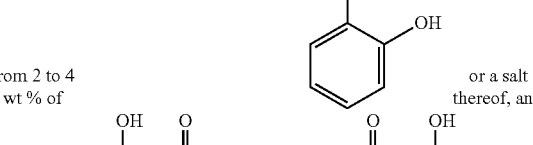

5. The preservative or anti-microbial system of claim 1, further comprising glycerin.

6. The preservative or anti-microbial system of claim 5, comprising 15 to 25 wt % of glycerin.

7. The preservative or anti-microbial system of claim 6, comprising 18 to 22 wt % of glycerin.

8. The preservative or anti-microbial system of claim 1, further comprising a secondary preservative or antimicrobial agent.

9. The preservative or antimicrobial system of claim 8, wherein the secondary preservative or antimicrobial agent is selected from the group consisting of at least one of iodopropynyl butylcarbamate, capylyl glycol, imidazolidinyl urea, a paraben, methylsothiazoline, chlorphenesin, or benzoic acid or any combination thereof.

10. The preservative or antimicrobial system of claim 9, comprising iodopropynyl butylcarbamate or capylyl glycol or both of iodopropynyl butylcarbamate and capylyl glycol.

11. The preservative or anti-microbial system of claim 10, comprising:
from 20 to 25% w/w of caprylyl glycol; and
from 70 to 80% w/w of the ester/esters of salicylic acid and glycerin.

12. The preservative or anti-microbial system of claim 11, comprising:
from 0.5 to 2% w/w of iodopropynyl butylcarbamate;
from 20 to 25% w/w of caprylyl glycol; and
from 70 to 80% w/w of the ester/esters of salicylic acid and glycerin.

13. The preservative or antimicrobial system of claim 9, comprising imidazolidinyl urea.

14. The preservative or anti-microbial system of claim 13, comprising:
from 20 to 25% w/w of imidazolidinyl urea; and
from 70 to 80% w/w of the ester/esters of salicylic acid and glycerin.

15. The preservative or anti-microbial system of claim 1, wherein said system is effective in inhibiting the growth of a gram-positive bacteria, a gram-negative bacteria, a yeast or a mold.

16. The preservative or anti-microbial system of claim 15, wherein the gram-positive bacteria is *Staphyloccus aureus* and/or *Staphylococcus epidermidis*, wherein the gram-negative bacteria is oxidative gram-gram negative bacteria selected from the group consisting of at least one of *Pseudomonas aeruginosa, Pseudomonas cepacia*, and/or *Pseudomonas putida*, wherein the gram-negative bacteria is fermentative gram-negative bacteria selected from the group consisting of *Escherichia coli, Klebsiella pneumonia*, and/or *Enterobacter aerogenes*, wherein the yeast is *Candida albicans*, and wherein the mold is *Aspergillus niger*.

17. The preservative or anti-microbial system of claim 1, wherein said system is substantially anhydrous.

18. The preservative or anti-microbial system of claim 1, wherein said system does not include salicylic acid and/or does not include a paraben.

19. The preservative or anti-microbial system of claim 1, wherein said system is comprised within a cosmetic formulation or a pharmaceutical formulation.

20. The preservative or anti-microbial system of claim 19, wherein said formulation is an emulsion, solution, or ointment.

21. The preservative or anti-microbial system of claim 1, wherein said system is a disinfectant formulation or a cleansing formulation.

22. A method of inhibiting the growth of a microorganism comprising contacting the microorganism with the preservative or anti-microbial systems of claim 1, wherein the growth of the microorganism is inhibited.

23. A method of inhibiting the growth of a microorganism in a cosmetic or pharmaceutical formulation comprising adding the preservative or anti-microbial system of claim 1 to said formulation, wherein growth of the microorganism in said formulation is inhibited.

24. A method of stabilizing an emulsion that includes caprylyl glycol comprising adding the preservative or anti-microbial system of claim 1 to the emulsion, wherein the emulsion is stabilized by the addition of said preservative or anti-microbial system.

* * * * *